(12) United States Patent
Asselin et al.

(10) Patent No.: US 9,770,855 B2
(45) Date of Patent: Sep. 26, 2017

(54) METHOD OF MANUFACTURING A SURGICAL INSTRUMENT OR PROSTHESIS

(75) Inventors: Henri Asselin, Wilmington, MA (US); Michael Reeve, Leeds (GB); Todd Beaupre, Wilmington, MA (US)

(73) Assignees: LAKE REGION MEDICAL, INC., Chaska, MN (US); DEPUY IRELAND UNLIMITED COMPANY, Cork (IE)

( * ) Notice: Subject to any disclaimer, the term of this patent is extended or adjusted under 35 U.S.C. 154(b) by 817 days.

(21) Appl. No.: 14/117,121

(22) PCT Filed: May 11, 2012

(86) PCT No.: PCT/GB2012/051061
§ 371 (c)(1),
(2), (4) Date: Jan. 19, 2015

(87) PCT Pub. No.: WO2012/153149
PCT Pub. Date: Nov. 15, 2012

(65) Prior Publication Data
US 2015/0174801 A1    Jun. 25, 2015

(30) Foreign Application Priority Data
May 12, 2011   (GB) .................................. 1107931.6

(51) Int. Cl.
*B29C 45/00* (2006.01)
*B29C 45/16* (2006.01)
(Continued)

(52) U.S. Cl.
CPC .......... *B29C 45/0003* (2013.01); *B29C 45/16* (2013.01); *A61B 2017/00526* (2013.01);
(Continued)

(58) Field of Classification Search
None
See application file for complete search history.

(56) References Cited

U.S. PATENT DOCUMENTS

| 4,760,972 A | 8/1988 | Sasaki |
| 5,694,268 A | 12/1997 | Dunfield |

(Continued)

FOREIGN PATENT DOCUMENTS

| CN | 1515387 A | 7/2004 |
| FR | 2386411 | 2/1980 |

(Continued)

OTHER PUBLICATIONS

PCT Int'l Search Report & Written Opinion PCT/GB2012/050317 Dated May 18, 2012, 10 pages.
(Continued)

*Primary Examiner* — Edmund Lee

(57) ABSTRACT

A method of manufacturing a surgical instrument or prosthesis and an injection moulded surgical instrument or prosthesis are described. A first material is injected into a first mould to form an interim component. A second material is injected into a second mould containing at least part of the interim component to form the surgical instrument or prosthesis such that portions of the first and second materials are exposed at the external surface of the surgical instrument or prosthesis. The first and second materials are visually distinct such that at least one exposed portion of the first or second material adjacent to an exposed portion of the other material forms a marking which is visible to a user.

11 Claims, 5 Drawing Sheets

(51) Int. Cl.
    *B29L 31/00*    (2006.01)
    *A61B 17/00*    (2006.01)
    *A61B 90/00*    (2016.01)

(52) U.S. Cl.
    CPC . *A61B 2090/3937* (2016.02); *A61F 2240/001* (2013.01); *B29C 2045/167* (2013.01); *B29L 2031/7532* (2013.01); *B29L 2031/7546* (2013.01); *Y10T 428/24802* (2015.01)

(56) References Cited

U.S. PATENT DOCUMENTS

| | | | |
|---|---|---|---|
| 6,248,007 | B1 | 6/2001 | deBlois |
| 6,368,536 | B1 | 4/2002 | Hoepfl et al. |
| 6,726,868 | B1 | 4/2004 | Panfili |
| 7,001,083 | B1 | 2/2006 | Nguyen |
| 7,647,084 | B2 | 1/2010 | Eghbal |
| 7,738,937 | B2 | 6/2010 | Coakley |
| 7,867,279 | B2 | 1/2011 | Hester |
| 8,372,030 | B2 | 2/2013 | Dixon |
| 8,496,690 | B2 | 7/2013 | Sixto |
| 8,662,299 | B2 | 3/2014 | Pratt |
| 2004/0155171 | A1 | 8/2004 | Kozlovski |
| 2005/0033237 | A1 | 2/2005 | Fentress |
| 2006/0157996 | A1 | 7/2006 | McRorie |
| 2007/0170608 | A1 | 7/2007 | Iatan |
| 2008/0083812 | A1 | 4/2008 | Scirica |
| 2009/0247987 | A1 | 10/2009 | Chevalier, Jr. |
| 2010/0180400 | A1 | 7/2010 | Pell |
| 2010/0274093 | A1 | 10/2010 | Shelton, IV |

FOREIGN PATENT DOCUMENTS

| | | |
|---|---|---|
| GB | 2110586 A | 6/1983 |
| GB | 2426953 A | 12/2006 |
| JP | 57140114 A | 8/1982 |
| JP | 58076243 A | 5/1983 |
| JP | 5092442 A | 4/1993 |
| JP | 05-035232 U | 5/1993 |
| JP | 2010214830 A | 9/2010 |
| WO | WO 9734740 A1 | 9/1997 |

OTHER PUBLICATIONS

GB Search Report GB1104842.8 Dated Jul. 1, 2011, 5 pages.
PCT International Search Report and Written Opinion PCT/GB2012/051061 dated Jul. 16, 2012.
UK Search Report GB1107931.6 dated Sep. 13, 2011.
Chinese Search Report for Corresponding Chinese Patent App. No. 201280022892.4, 3 Pages.
Japanese Search Report for Japanese Patent Application No. 2014-509840, Mailed Dec. 15, 2015, 5 pages.

METHOD OF MANUFACTURING A SURGICAL INSTRUMENT OR PROSTHESIS

CROSS REFERENCE TO RELATED APPLICATION

This application is a National Stage 35 U.S.C. 371 of International Patent Application PCT/GB2012/051061 filed May 11, 2012.

BACKGROUND OF THE INVENTION

The present invention relates to a manufacturing method and a product produced by the manufacturing method. In particular, the present invention relates to methods of making surgical instruments and prostheses.

Surgical instruments and prostheses are typically formed from a relatively small number of materials, which are selected for their properties, including biocompatibility, strength and resilience. Typical materials include metals such as stainless steel and plastics. The chosen materials, and the methods by which the instruments are formed, vary according to the particular function of the instrument or prosthesis.

It is a common requirement of surgical instruments and prostheses that they are provided with markings to aid their use by surgeons. Markings may include gauge lines, numerals, letters or any other form of symbol. For components formed from plastic it is known to form markings by applying dyes or paints to the surface of the instrument, or into recesses within the surface. Alternatively, markings may be etched onto the instrument. Such additional processing steps increase the cost of manufacturing surgical instruments. Additionally, the markings produced may be prone to damage during cleaning, which may make the instrument or prosthesis hard to clean.

It is an object of embodiments of the present invention to obviate or mitigate one or more of the problems associated with the prior art, whether identified herein or elsewhere.

BRIEF SUMMARY OF THE INVENTION

According to a first aspect of the present invention there is provided a method of manufacturing a surgical instrument or prosthesis comprising: injecting a first material into a first mould to form an interim component; and injecting a second material into a second mould containing at least part of the interim component to form the surgical instrument or prosthesis such that portions of the first and second materials are exposed at the external surface of the surgical instrument or prosthesis; wherein the first and second materials are visually distinct such that at least one exposed portion of the first or second material adjacent to an exposed portion of the other material forms a marking which is visible to a user.

An advantage of the first aspect of the present invention is that markings may be produced on a surface of a surgical instrument or prosthesis that are relatively resilient to damage caused when cleaning the instrument or prosthesis. This is because the markings are formed from a similar plastic to the remainder of the instrument and so form an integral part of the instrument, in contrast to markings applied to the surface of an instrument using a dye or paint, which may be erased during cleaning. As the plastics used are visually distinct, for instance different colours, the markings may be highly visible to a surgeon.

In the step of injecting a second material into a second mould the second material may partially or fully surround at least one portion of the interim component such that the first material in that portion forms a marking.

In the step of injecting a second material into a second mould the second material may be deposited upon a selected portion of the surface of the interim component such that the second material in that portion forms a marking.

The interim component may incorporate at least one aperture extending through a portion of the interim component, and wherein said step of injecting the second material comprises the second material flowing through the aperture to the selected portion of the surface of the interim component.

The interim component may comprise at least one channel arranged to direct the flow of the second material during the step of injecting the second material, the at least one channel communicating with the at least one aperture.

The selected portion of the surface of the interim component may comprise a recess arranged to receive the second material to form the marking.

The recess may further comprise at least one blind hole spaced apart from the surface of the interim component surrounding the recess, the blind hole being arranged to receive gas within the recess during the step of injecting a second material into a second mould.

The selected portion of the surface of the interim component may be on an exterior surface of the interim component.

The second mould may be arranged to seal to the interim component surrounding the selected portion of the surface of the interim component to define the edge of the marking.

The first and second materials may be different colours.

The marking may be arranged to be recessed, flush or proud of the surrounding external surface of the surgical instrument or prosthesis.

The first and second materials may comprise plastics. The first and second plastics may have substantially similar structural properties. The first and second plastics may comprise the same plastic. At least one of the first and second plastics may further comprise at least one additive. The or each plastic may comprise a high or ultra high performance polymer, or silicone.

According to a second aspect of the present invention there is provided an injection moulded surgical instrument or prosthesis comprising: an injection moulded body having an external surface, said external surface comprising at least one exposed first portion formed from a first material in a first injection moulding step and at least one exposed second portion formed from a second material in a second injection moulding step; wherein the first and second materials are visually distinct such that at least one of said first and second portions forms a marking which is visible to a user.

BRIEF DESCRIPTION OF THE DRAWINGS

The present invention will now be described, by way of example only, with reference to the accompanying figures, in which.

DETAILED DESCRIPTION OF THE INVENTION

Figure 1:
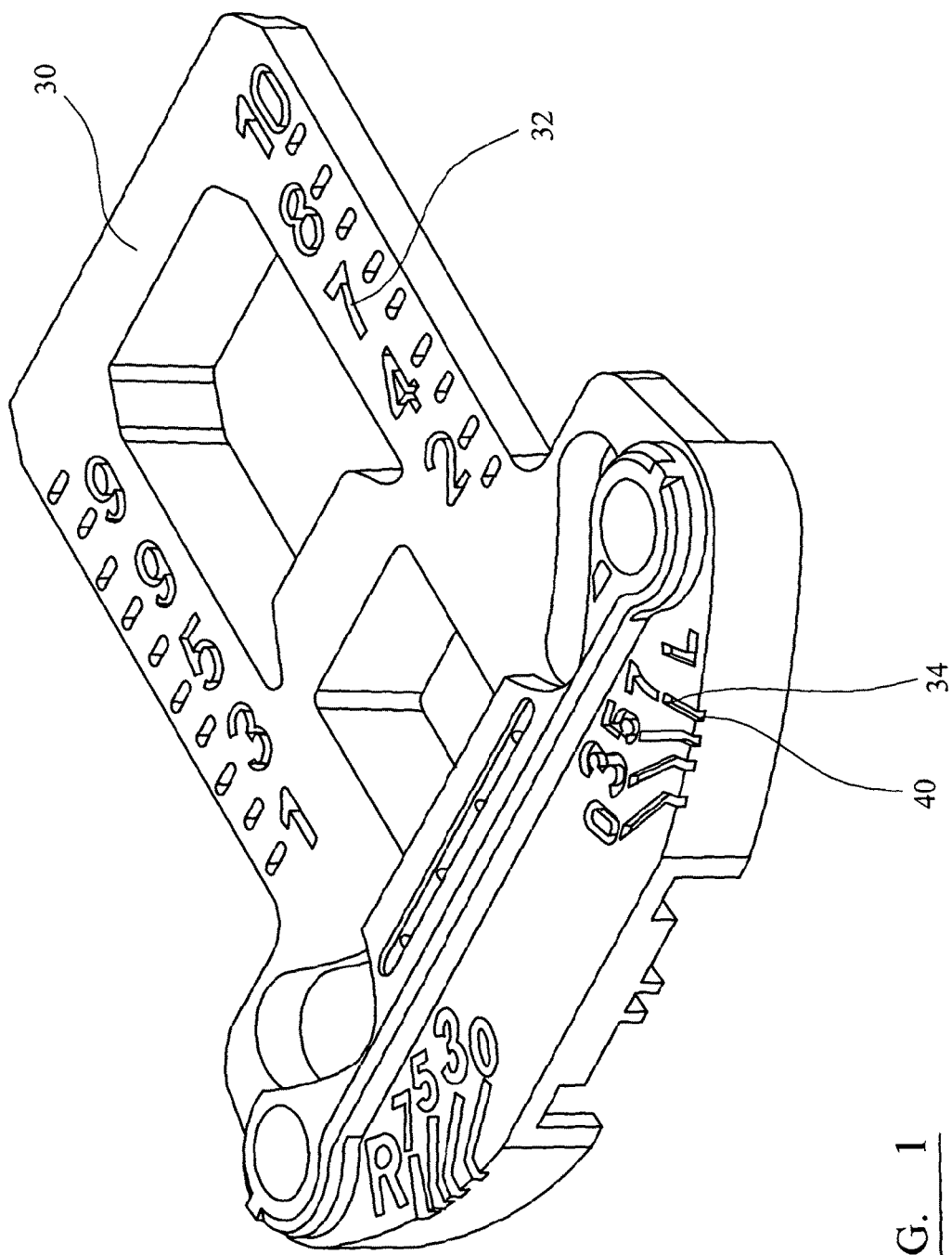
FIG. 1 is a perspective view of part of an interim component formed using a manufacturing method in accordance with an embodiment of the present invention.

It is known to manufacture products, including surgical instruments and prostheses, through injection moulding. A material such as thermoplastic or thermosetting plastic is heated and mixed to ensure a uniform consistency. The molten material is forced under pressure into a mould cavity where it cools and hardens. The amount of material required to fill the cavities of the mould is called a shot.

It is known to use injection moulding to apply a layer of a plastic material over part or the whole of an existing interim component. This technique may be referred to as over-moulding or two shot moulding. One known application of this is to couple together two different forms of plastic having different material properties. For example, a toothbrush may comprise a first, stiff plastic forming the body of a handle, and a second, softer plastic forming a hand grip. Two shot moulding is also known for coating other materials such as metals with plastic, and for joining together two separate components.

In accordance with an embodiment of the present invention, a two shot injection moulding process can be used to generate markings on surgical instruments or prostheses which are visible to a user and resistant to damage during routine cleaning. In a first injection moulding step an interim component comprising the body of the instrument or prosthesis is formed. In a second injection moulding step, part or the whole of the interim component is inserted into a second mould which seals to the interim component and defines regions on the surface of the interim component where marks such as symbols and lines are to be formed. A plastic material which is visually distinct from the plastic material used in the first injection moulding step is injected into the mould in the region of the markings.

It may be that exactly the same plastic is used in the first and second injection moulding steps, albeit treated in some way to be visually distinct, for instance by being a different colour. However, it may be that different, though similar, plastics are used. In certain applications, dissimilar plastics may be used, though typically the same or similar plastics will be required for functional reasons associated with the use of the instrument or prosthesis. By "similar" it is intended that the plastics used in each injection moulding step are generally the same, with similar chemical, structural or function properties. In particular embodiments of the present invention, where different but similar plastics are used, each plastic may be within the group of plastics known in the plastics industry as "high performance polymers" and "ultra high performance polymers" as these generally have high resistance to chemicals, moisture and temperature as well as high stiffness. Alternatively, types of silicone may be used. One option for using two shot moulding to form markings is to form the body of the instrument or prosthesis from a glass filled plastic and the marking from the same plastic, without glass fill. Alternatively, the plastics may be substantially the same as one another, differing only in the particular dye which is incorporated into the plastic mix.

The regions where markings are to be formed upon the surface of the interim component may be selected portions of a flat surface of the interim component. The shape and size of the region (including the height of the marking above the surrounding surface of the interim component) may be defined by the shape of the mould and how it seals to the interim component. Alternatively, the marking regions may be partly or fully defined by recesses in the surface of the interim component. Where recesses are used, the mould may seal to the interim component such that the second plastic material is recessed relative to the surrounding surface of the interim component. Alternatively, the markings may be flush with the surrounding surface or stand proud of the surrounding surface.

In order to ensure that the second plastic material can pass to the required regions on the surface of the interim component, one or more channel may be defined within the interim component leading to the marking regions. For instance, where a marking is to be formed on a first surface, a channel may be formed on a reverse surface of the interim component, passing underneath the marking region. A fill hole may connect the channel to the marking region such that injected plastic supplied to the channel can pass through the fill hole to the marking region. Advantageously, a single channel may be provided with multiple fill holes coupling to respective marking regions such that a single injection port in the second injection moulding step can be used to form multiple markings.

Referring now to FIG. 1, this illustrates a perspective view of an interim component part way through a manufacturing process in accordance with an embodiment of the invention. The interim component comprises an injection moulding plastic component that is intended to be over-moulded to form a surgical instrument or prostheses. It can be seen that the interim component of FIG. 1 comprises a single body 30 which may generally comprise the majority of the structure of the surgical instrument (or at least that part of the whole surgical instrument formed through injection moulding). Set into the surface of the body 30 are a series of recesses, for instance recess 32. It can be seen that some of the recesses 32 form numbers and letters, and some form lines and other shapes. The recesses 32 define regions on the surface of body 30 where markings are to be formed.

At the base of each recess 32 is at least one fill hole 34. It will be appreciated that fill holes 34 are only visible in certain of the recesses 32 in the view of FIG. 1 owing to the perspective view of the interim component. Additionally, some or all of the recesses 32 may comprises blind holes 40. Fill holes 32 extend fully through the interim component 30. The blind holes 40 are closed at one end and from smaller recesses at the base of the marking recesses 32. One fill hole 32 and one blind hole 40 are identified in FIG. 1. It will be appreciated that in the perspective view of FIG. 1 and the plane view of FIG. 2 the fill holes 32 and the blind holes 40 are hard to distinguish. The difference between the fill holes 32 and the blind holes 40 can be more clearly seen in the cross sectional views of FIGS. 4 to 8 described below.

Figure 2:
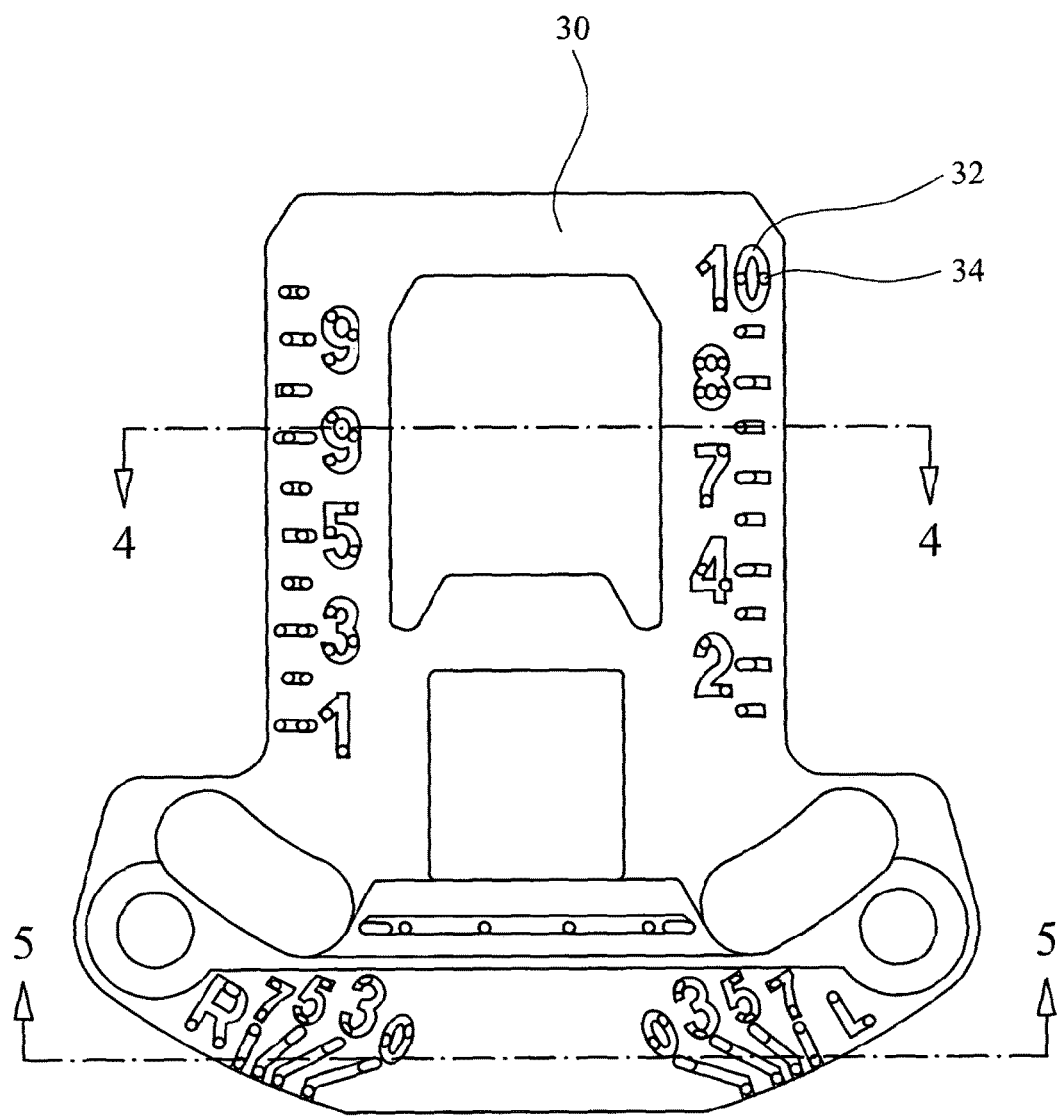
FIG. 2 is a top view of the interim component of FIG. 1.
Figure 3:
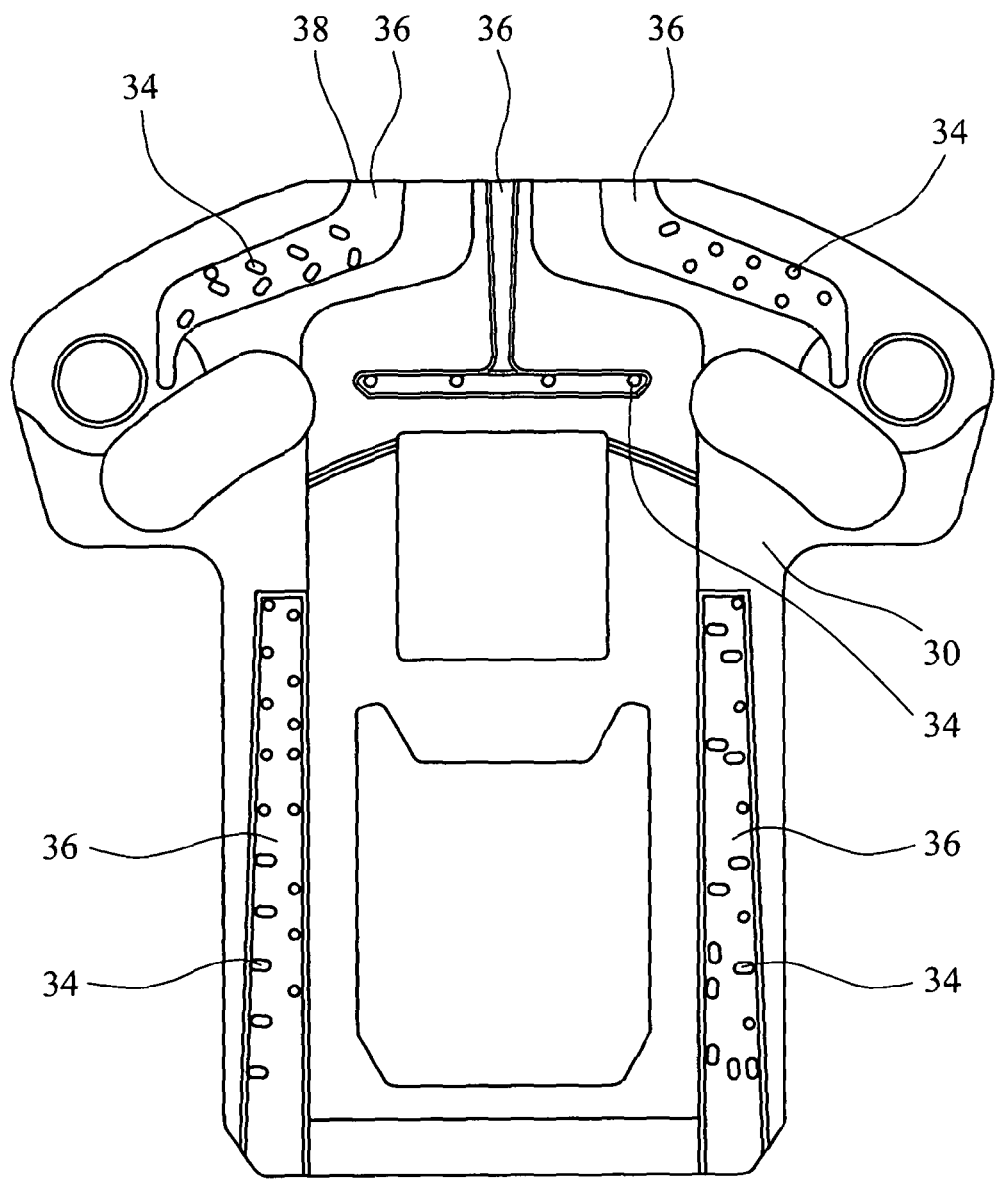
FIG. 3 is a bottom view of the interim component of FIG. 1.

Referring also to the top view of the interim component in FIG. 2, it can be seen that each recess 32 connects with at least one fill hole 34. Referring to FIG. 3, this is a bottom view of the interim component 30 of FIG. 1. The base of the interim component 30 defines a number of channels 36 which each extend from the exterior edge 38 of the interim component to a group of fill holes 34. In alternative embodiments of the present invention a channel 36 could connect with only a single fill hole. Each channel 36 is open on one face (which will be closed off by the side of the second mould during the second injection moulding step) and is of sufficient depth to allow plastic to flow through to each fill hole 34, and hence to each recess 32.

Figure 4:
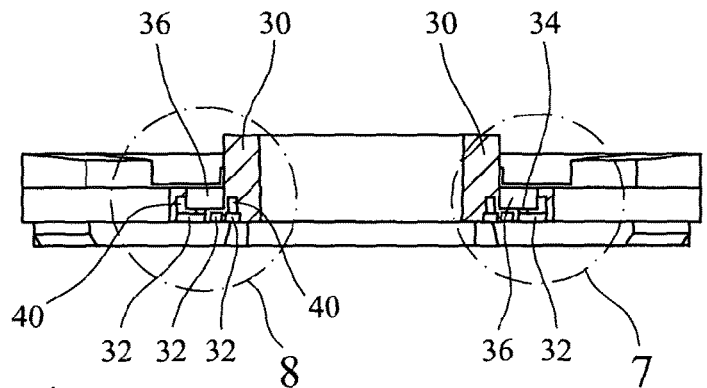
FIG. 4 is a cross sectional view of the interim component of FIG. 2 along the line 4:4 in the direction of the arrows.
Figure 5:
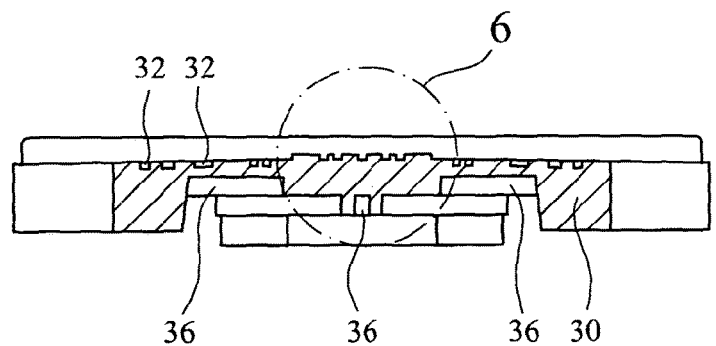
FIG. 5 is a cross sectional view of the interim component of FIG. 2 along the line 5:5 in the direction of the arrows.
Figure 6:
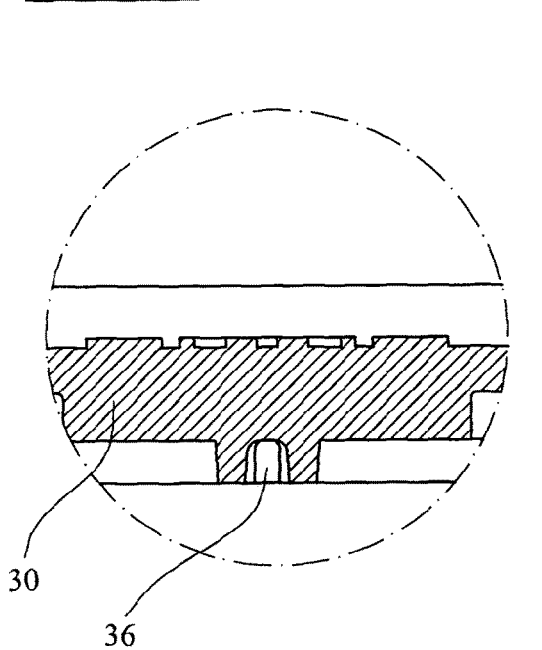
FIG. 6 is an enlargement of region 6 of FIG. 5.
Figure 7:
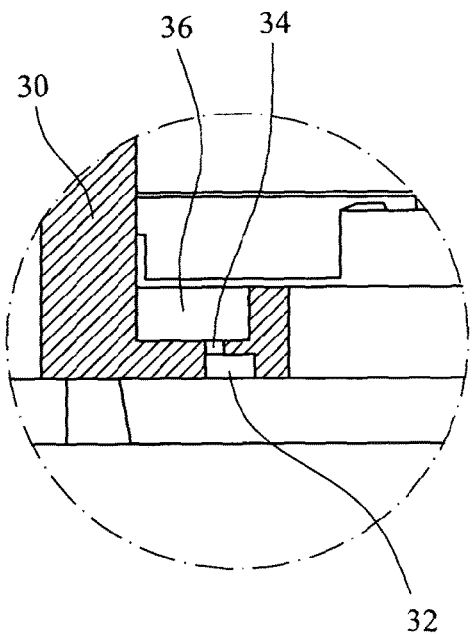
FIG. 7 is an enlargement of region 7 of FIG. 4.

FIGS. 4 and 5, together with the enlargements of FIGS. 6 and 7, illustrate cross sectional views of the interim component. It can be seen particularly in the enlargement of FIG. 7 that the channels 36 extend through a significant depth of the body 30, and the fill holes 34 are narrower and shallower than the channels 36 before opening out into the recesses 32. FIG. 7 illustrates in an enlarged view a portion of the cross section of FIG. 4 in which the relative dimensions of the channel 36, the fill hole 34 recess marking 32 can be clearly seen. FIG. 6 illustrates in an enlarged view a portion of the cross section of FIG. 5 showing part of a channel 36 passing through a region of the interim component 30 which does not include any marking recesses 32. It will be understood that the channels 36 must extend from an exterior edge 38 of the interim component 30 to wherever markings are required. FIG. 3 illustrates that multiple channels 36 may be required to supply plastic to all of the marking recesses 32 in the second injection moulding step. In alternative embodiments of the present invention, the mould for the second injection moulding step may be arranged to supply plastic directly to a face of the interim component 30 and so it may not be necessary to have the channels extending all of the way to the edge 38 of the interim component 30.

Figure 8:
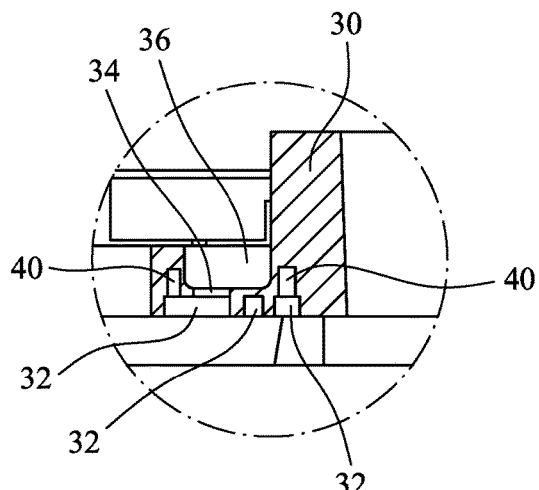
FIG. 8 is an enlargement of region 8 of FIG. 4.
Figure 9:
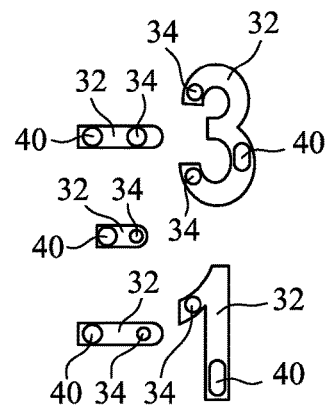
FIG. 9 is an enlarged view of some of the markings shown in FIG. 2.

Referring now to FIG. 8, this illustrates an enlarged portion of the cross section of FIG. 4 allowing a pair of blind holes 40 to be seen adjacent to a fill hole 34. During the second injection moulding step air within the recesses 32 is generally driven out between the surface of the mould and the interim component 30. However, if air is trapped this could prevent a recess 32 from being correctly filled with the second plastic. This could prevent a continuous surface formed from the second plastic being formed for that particular marking in the finished surgical instrument or prosthesis. A blind hole 40 accommodates the trapped air and allows the second plastic to fully flow throughout the recess 32. It will be appreciated that blind holes 40 may not be required for all recesses 32, particularly small recesses or large recesses with separate air escape channels. Referring to FIG. 9, this illustrates an enlarged portion of the top view of the interim component of FIG. 2. Five recesses 32 are illustrated, including two numerals and three dashes. Each recess includes at least one fill hole 34 and at least one blind hole 40. It has been found that blind holes 40 are particularly useful in the case of recesses 32 having two fill holes 34 filling the recess from either end (for example, numeral "3") or where the recess 32 is elongated and is filled by a fill hole 32 towards one end (for example, numeral "1").

Figure 10:
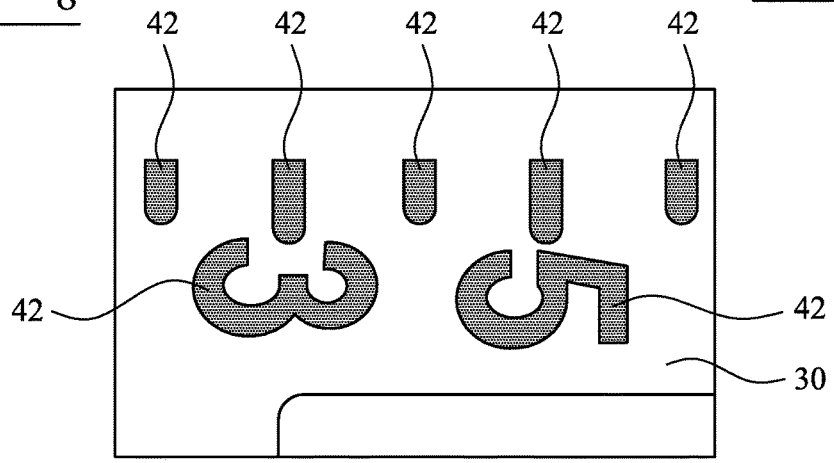
FIG. 10 is a view of part of the top of a surgical instrument formed from the interim component of FIG. 1.
Figure 11:
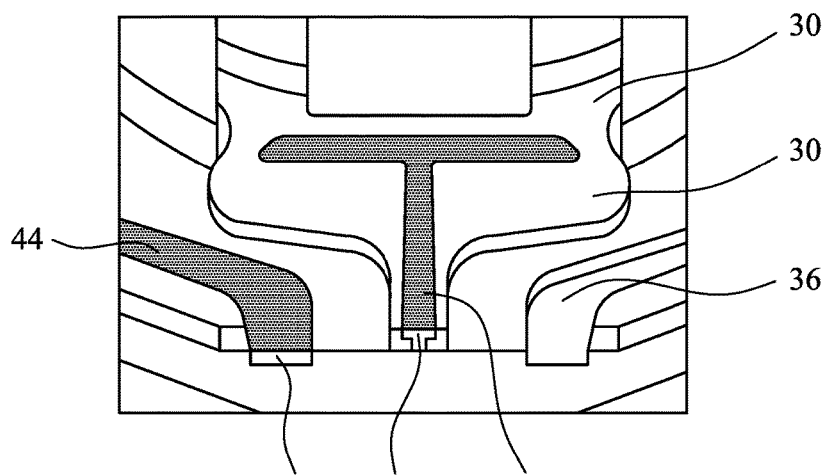
FIG. 11 is a view of part of the bottom of a surgical instrument formed from the interim component of FIG. 1.

Referring to FIGS. 10 and 11 this respectively illustrate portions of a top surface and a bottom surface of a surgical instrument formed in accordance with an embodiment of the present invention using the interim component 30 of FIG. 1 in a second injection moulding step. In FIG. 10 markings 42 are visible, including two numerals and dashes. It can be seen that a first marking (numeral "5") is flush with the surrounding instrument. Specifically, the first marking was formed by injecting the second plastic through a fill hole into a recess that was sealed flush to the surrounding first plastic by the second mould having a flat portion. A second marking (numeral "3") stands proud with the surrounding instrument as the mould in the second injection moulding step was sealed to the surrounding first plastic, and the second mould includes a recess having the shape of the numeral. In FIG. 11 two filled channels 44 are visible where the second plastic material has been injected into a portion of the second mould along an edge 38 of the mould such that the second plastic flows to portions of the channel 36 where fill holes 34 are provided. For comparison, one channel 36 is shown unfilled with the second plastic material.

The visual quality of the markings on a completed surgical instrument or prosthesis are affected by a ranged of factors. These include the particular materials used, the width and depth of the markings (that is, the recesses and/or the portion of the marking protruding from the surrounding plastic), the dimensions, positions and number of the fill holes, the dimensions of the channels, the dimensions, positions and number of the blind holes and the wall thickness and accuracy of the interim component formed in the first injection moulding step.

As an example of suitable plastics, Avaspire (RTM) AV 651 GF30 BK95 may be used in the first injection moulding step to form the interim component. This is Polyaryletherketone reinforced with 30% glass fibre manufactured by Solvay Advanced Polymers and coloured black. Avaspire (RTM) AV 651 GF30 BG20 may be used in the second injection moulding step to form the markings. This is generally the same as the first plastic except coloured beige.

It has been found that good quality markings can be formed if they have a minimum width of no less than 0.25 mm, for instance approximately 0.43 mm. Similarly, it has been found that a suitable maximum marking width is no more than 2 mm, for instance approximately 1 mm. It has been found that good quality markings can be formed if they have a minimum depth of no less than 0.1 mm, for instance approximately 0.24 mm.

It has been found that to ensure adequate flow of plastic to the markings the fill holes should have a maximum ratio of diameter to length of 2, for example a diameter of 0.5 mm and a length of 0.25 mm. The maximum diameter of the fill hole is limited by the shape and size of the recess to be filled in the second injection moulding step. However, it is desirable to ensure that within the recess the fill hole is spaced apart from the sides of the recess to ensure good mechanical retention of the material injected in the second injection moulding step. The fill holes may have a minimum diameter of no less than 0.25 mm, for example approximately 0.3 mm. The fill holes may have a maximum diameter of no more than 0.75 mm, for instance approximately 0.530 mm. The fill holes may have a minimum length of no less than 0.25 mm, for instance approximately 0.35 mm. The fill holes may have a maximum length of no more than 2 mm, for instance approximately 1.0 mm. It will be appreciated that the dimensions, number and positions of the fill holes are largely dependent upon the shape of the marking to be formed and the volume of material required to form the markings, in combination with the parameters of the second injection moulding step, including the injection pressure.

In an alternative embodiment, it may be that the interim component formed from the first plastic includes at least one marking and the second injection moulding step is arranged to form the external structure of the instrument or prosthesis surrounding the marking and leaving the marking uncovered. The second plastic may be arranged to partially or fully surround the marking. Markings may also be formed from portions of both the first and second plastics which are exposed at the external surface of the instrument or prosthesis and visible relative to the surrounding second or first plastic respectively.

While the embodiment of the present invention described above relates to a surgical instrument and a method of manufacturing such an instrument, the invention defined by the claims is not limited to this. The same manufacturing technique may also be applied to manufacturing surgical prostheses. In particular, the manufacturing technique described above is generally applicable wherever there is a need to apply robust markings to plastic surgical instruments or prostheses.

Other applications of, and modifications to, the present invention will be readily apparent to the appropriately skilled person from the teaching herein, without departing from the scope of the appended claims.

The invention claimed is:

1. A method of manufacturing a surgical instrument or prosthesis, comprising the steps of:
   injecting a first material into a first mold to form an interim component; and
   injecting a second material into a second mold containing at least part of the interim component to form the surgical instrument or prosthesis such that portions of the first and second materials are exposed at the external surface of the surgical instrument or prosthesis;
   wherein the first and second materials are visually distinct such that at least one exposed portion of the first or second material adjacent to an exposed portion of the other material forms a marking which is visible to a user,
   wherein in the step of injecting the second material into the second mold comprises injecting the second material such that the second material is deposited upon a selected portion of the surface of the interim component such that the second material in contact with the selected portion forms a marking;
   wherein the selected portion of the surface of the interim component has a recess arranged to receive the second material to form the marking;
   wherein the recess communicates with at least one blind hole formed in the interim component, the at least one blind hole spaced apart from the surface of the interim component surrounding the recess; and
   wherein the blind hole is arranged to receive gas within the recess during the step of injecting the second material into the second mold.

2. The method of claim 1, wherein in the step of injecting the second material into the second mold comprises injecting the second material such that it partially or fully surrounds at least one portion of the interim component such that the first material in that portion forms a marking.

3. The method of claim 1, wherein the interim component has at least one aperture extending through a portion of the interim component, and wherein step of injecting the second material into the second mold comprises injecting the second material such that the second material flows through the aperture to the selected portion of the surface of the interim component.

4. The method of claim 3, wherein the interim component has at least one channel configured to direct the flow of the second material during the step of injecting the second material, the at least one channel communicating with the at least one aperture.

5. The method of claim 1, wherein the selected portion of the surface of the interim component is on an exterior surface of the interim component.

6. The method of claim 1, wherein the second mold is arranged to seal to the interim component surrounding the selected portion of the surface of the interim component to define the edge of the marking.

7. The method of claim 1, wherein the first and second materials are different colors.

8. The method of claim 1, wherein the marking is arranged to be recessed, flush or proud of the surrounding external surface of the surgical instrument or prosthesis.

9. The method of claim 1, wherein the first and second materials comprise a plastic material.

10. The method of claim 9, wherein the first and second plastics comprise the same plastic.

11. The method of claim 10, wherein at least one of the first and second plastics further comprise at least one additive.

* * * * *